United States Patent
Graham

(10) Patent No.: US 9,791,080 B2
(45) Date of Patent: Oct. 17, 2017

(54) MICROFLUIDIC INTERCONNECT

(71) Applicant: IDEX Health & Science LLC, Oak Harbor, WA (US)

(72) Inventor: Craig Graham, Anacortes, WA (US)

(73) Assignee: IDEX Health & Science LLC, Oak Harbor, WA (US)

( * ) Notice: Subject to any disclaimer, the term of this patent is extended or adjusted under 35 U.S.C. 154(b) by 459 days.

(21) Appl. No.: 13/686,260

(22) Filed: Nov. 27, 2012

(65) Prior Publication Data

US 2013/0234432 A1   Sep. 12, 2013

(51) Int. Cl.
*F16L 37/244*   (2006.01)
*B01L 3/00*   (2006.01)
(Continued)

(52) U.S. Cl.
CPC ....... *F16L 37/244* (2013.01); *B01L 3/502715* (2013.01); *B01L 3/563* (2013.01);
(Continued)

(58) Field of Classification Search
CPC ......... B01L 2200/025; B01L 2200/027; B01L 2200/0631; F16L 15/08; F16L 19/0237; F16L 19/065; F16L 21/00; F16L 37/244
(Continued)

(56) References Cited

U.S. PATENT DOCUMENTS 697,036 A * 4/1902 Stern ...................... B65D 39/00
215/355
2,048,852 A   7/1936 Dumas
(Continued)

FOREIGN PATENT DOCUMENTS

EP         1880765 A2    1/2008
WO    WO 90/05295       5/1990
(Continued)

OTHER PUBLICATIONS

Puntambekar and Ahn, J. Micromech. Microeng. 12:35-40, 2002.
(Continued)

*Primary Examiner* — James M Hewitt
(74) *Attorney, Agent, or Firm* — Vinson & Elkins LLP

(57) ABSTRACT

A microfluidic interconnect system and method for assembly thereof is described. The microfluidic interconnect has a port and a seal, with the port having a reverse taper. The port has a first port end, a second port end, and an inner port surface with a tapered portion. Each port end has an opening with a diameter, and in certain embodiments, the diameter of the first port end is smaller than the diameter of the second port end. The seal has a first end and a second end, and each seal end has a rim and an opening with an inner diameter and an outer diameter. The seal also has an inner surface and an outer surface, where in certain embodiments, each surface has a tapered portion. In certain embodiments, the inner diameter of the first seal end is equal to or larger than the inner diameter of the second seal end, the outer diameter of the first seal end is equal to or smaller than the outer diameter of the second seal end, and the outer diameter of the second seal end is larger than the outer diameter of each port end. In certain embodiments, a tube is slidably coupled to the inner surface of the seal, and the tube has an outer diameter that is equal to or larger than the inner diameter of the second seal end.

32 Claims, 12 Drawing Sheets

(51) Int. Cl.
*F16L 15/08* (2006.01)
*F16L 19/02* (2006.01)
*F16L 19/065* (2006.01)
*F16L 21/00* (2006.01)
*G01N 30/88* (2006.01)
*G01N 30/60* (2006.01)

(52) U.S. Cl.
CPC ........... *F16L 15/08* (2013.01); *F16L 19/0237* (2013.01); *F16L 19/065* (2013.01); *F16L 21/00* (2013.01); *G01N 30/88* (2013.01); *B01L 2200/025* (2013.01); *B01L 2200/027* (2013.01); *B01L 2200/0631* (2013.01); *B01L 2200/0689* (2013.01); *B01L 2300/0832* (2013.01); *B01L 2300/0851* (2013.01); *G01N 30/6026* (2013.01); *G01N 30/6095* (2013.01); *Y10T 29/49826* (2015.01)

(58) Field of Classification Search
USPC ................ 285/9.2, 137.11; 277/606, 355
See application file for complete search history.

(56) References Cited

U.S. PATENT DOCUMENTS

| | | | |
|---|---|---|---|
| 3,640,552 A | 2/1972 | Demler, Sr. et al. | |
| 3,871,770 A | 3/1975 | von Behrens et al. | |
| 3,888,523 A | 6/1975 | Bartholomew | |
| 4,555,050 A | 11/1985 | Schiefer et al. | |
| 4,787,656 A * | 11/1988 | Ryder ..................... | 285/148.23 |
| 4,819,684 A | 4/1989 | Zaugg et al. | |
| 4,895,500 A | 1/1990 | Hok et al. | |
| 4,991,883 A | 2/1991 | Worden | |
| 5,170,286 A | 12/1992 | Zimmerberg | |
| 5,232,669 A | 8/1993 | Pardinas | |
| 5,312,377 A | 5/1994 | Dalton | |
| 5,343,909 A | 9/1994 | Goodman | |
| 5,482,628 A * | 1/1996 | Schick .................. | B01D 15/22 210/198.2 |
| 5,525,303 A | 6/1996 | Ford | |
| 5,730,943 A | 3/1998 | Ford | |
| 5,736,036 A | 4/1998 | Upchurch et al. | |
| 5,890,745 A | 4/1999 | Kovacs | |
| 6,045,162 A | 4/2000 | Haibara | |
| 6,095,572 A | 8/2000 | Ford | |
| 6,120,666 A | 9/2000 | Jacobson et al. | |
| 6,162,357 A | 12/2000 | Pakki et al. | |
| 6,209,928 B1 | 4/2001 | Benett et al. | |
| 6,273,478 B1 | 8/2001 | Benett et al. | |
| 6,290,791 B1 | 9/2001 | Shaw et al. | |
| 6,309,891 B1 | 10/2001 | Shalon et al. | |
| 6,344,034 B1 | 2/2002 | Sudo et al. | |
| 6,390,127 B2 | 5/2002 | Schick | |
| 6,443,179 B1 | 9/2002 | Benavides et al. | |
| 6,533,553 B2 | 3/2003 | Caren | |
| 6,595,964 B2 | 7/2003 | Finley et al. | |
| 6,626,468 B2 | 9/2003 | Ogawa | |
| 6,672,629 B2 | 1/2004 | Tai et al. | |
| 6,698,798 B2 | 3/2004 | Tai et al. | |
| 6,767,341 B2 | 7/2004 | Cho | |
| 6,841,130 B2 | 1/2005 | Lehtinen et al. | |
| 6,951,632 B2 | 10/2005 | Unger et al. | |
| 6,981,720 B2 | 1/2006 | White et al. | |
| 7,144,502 B2 | 12/2006 | Fermier | |
| 7,182,371 B1 | 2/2007 | Renzi | |
| 7,311,502 B2 | 12/2007 | Gerhardt | |
| 7,311,882 B1 | 12/2007 | Renzi | |
| 7,338,088 B2 * | 3/2008 | Salven et al. .............. | 285/124.3 |
| 7,351,380 B2 * | 4/2008 | Simmons et al. ........... | 422/502 |
| 7,475,916 B2 * | 1/2009 | Muller et al. .............. | 285/332.1 |
| 7,641,242 B2 | 1/2010 | Van Pelt | |
| 7,749,916 B2 | 7/2010 | Wong et al. | |
| 8,109,538 B2 | 2/2012 | Helstern et al. | |
| 8,162,357 B2 | 4/2012 | Kahl et al. | |
| 8,173,070 B2 | 5/2012 | Gerhardt | |
| 8,261,927 B1 * | 9/2012 | Volzke et al. ................ | 220/287 |
| 2002/0117517 A1 | 8/2002 | Unger et al. | |
| 2003/0173781 A1 | 9/2003 | Dodgson et al. | |
| 2007/0132241 A1 | 6/2007 | Mueller | |
| 2010/0320748 A1 | 12/2010 | Van't Oever et al. | |
| 2010/0322826 A1 | 12/2010 | Locascio et al. | |
| 2012/0024411 A1 | 2/2012 | Hahn et al. | |
| 2012/0031820 A1 | 2/2012 | Reinhardt | |
| 2012/0223520 A1 | 9/2012 | Graham | |
| 2012/0223522 A1 | 9/2012 | Graham | |
| 2013/0098481 A1 | 4/2013 | Delamarche et al. | |

FOREIGN PATENT DOCUMENTS

| | | |
|---|---|---|
| WO | WO 99/63260 | 12/1999 |
| WO | WO 00/21659 | 4/2000 |
| WO | WO 01/30490 | 5/2001 |
| WO | WO 2012/153668 A1 | 11/2012 |

OTHER PUBLICATIONS

Pattekar and Kothare, J. Micromech. Microeng. 13:337-345, 2003.
International Search Report and Written Opinion, International Patent Application No. PCT/US2013/071936, Feb. 19, 2014.
Co-Pending U.S. Appl. No. 13/668,011, filed Nov. 2, 2012.
Co-Pending U.S. Appl. No. 61/732,163, filed Nov. 6, 2012.

* cited by examiner

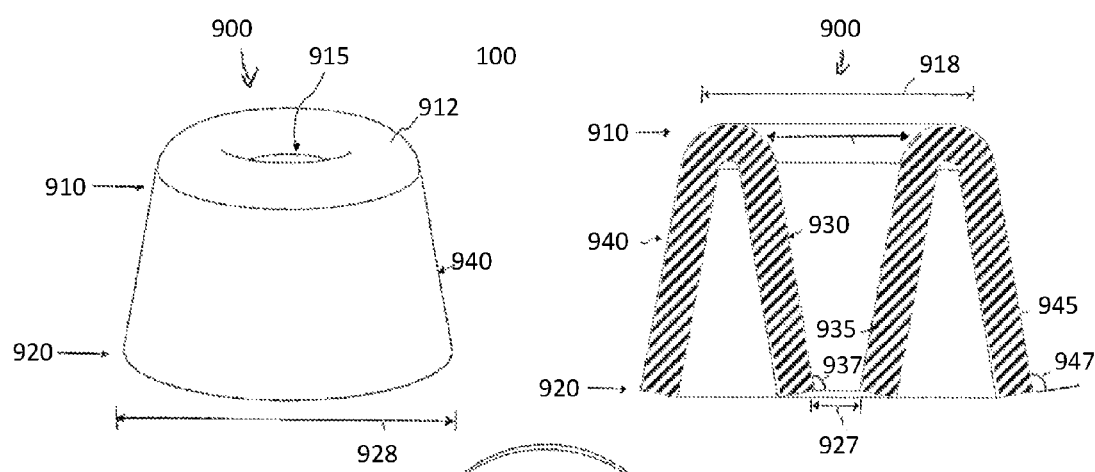
FIG. 12A
FIG. 12C
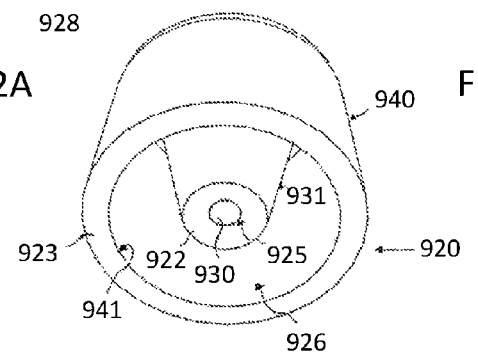
FIG. 12B

MICROFLUIDIC INTERCONNECT

CROSS-REFERENCE TO RELATED APPLICATION

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

Field of the Invention

This invention relates generally to an improved interconnect for use with microfluidic systems, and relates more particularly to an interconnect having a port with a reverse taper.

Description of the Related Art

The use of MEMS (Micro Electro-Mechanical System) devices continues to grow. Many companies are developing products which use MEMS devices. These devices can assume many different forms and utilize many different technologies. Open fluidic MEMS devices typically require one or more interconnects to connect the MEMS device to peripheral devices, such as components in liquid chromatography (LC) systems. LC and related technologies, and associated tubing and fittings, are discussed in U.S. patent application Ser. Nos. 13/038,110, 13/206,873, and 13/292,667, each of which is incorporated herein by reference.

Liquid chromatography (LC), ion chromatography (IC) and gas chromatography (GC) are well-known techniques for separating the constituent elements in a given sample. In a conventional LC system, a liquid solvent (referred to as the "mobile phase") is introduced from a reservoir and is pumped through the LC system. The mobile phase exits the pump under pressure. The mobile phase then travels via tubing to a sample injection valve. As the name suggests, the sample injection valve allows an operator to inject a sample into the LC system, where the sample will be carried along with the mobile phase.

In a conventional LC system, the sample and mobile phase pass through one or more filters and often a guard column before coming to the column. A typical column usually consists of a piece of tubing which has been packed with a "packing" material. The "packing" consists of the particulate material "packed" inside the column. It usually consists of silica- or polymer-based particles, which are often chemically bonded with a chemical functionality. When the sample is carried through the column (along with the mobile phase), the various components in the sample migrate through the packing within the column at different rates (i.e., there is differential migration of the solutes). In other words, the various components in a sample will move through the column at different rates. Because of the different rates of movement, the components gradually separate as they move through the column. Differential migration is affected by factors such as the composition of the mobile phase, the composition of the stationary phase (i.e., the material with which the column is "packed"), and the temperature at which the separation takes place. Thus, such factors will influence the separation of the sample's various components.

Once the sample (with its components now separated) leaves the column, it flows with the mobile phase past a detector, which can be built using MEMS technology. The detector detects the presence of specific molecules or compounds. Two general types of detectors are typically used in LC applications. One type measures a change in some overall physical property of the mobile phase and the sample (such as their refractive index). The other type measures only some property of the sample (such as the absorption of ultraviolet radiation). In essence, a typical detector in a LC system can measure and provide an output in terms of mass per unit of volume (such as grams per milliliter) or mass per unit of time (such as grams per second) of the sample's components. From such an output signal, a "chromatogram" can be provided; the chromatogram can then be used by an operator to determine the chemical components present in the sample. Additionally, LC systems may utilize mass spectrometric detection for identification and quantification of the sample, either in addition to, or as an alternative to, the conventional detectors described previously. Ion chromatography relies on the detection of ions in solution, so most metallic materials in the flow path can create interference in the detection scheme, as they create background ions.

In addition to the above components, a LC system will often include filters, check valves, a guard column, or the like in order to prevent contamination of the sample or damage to the LC system. For example, an inlet solvent filter may be used to filter out particles from the solvent (or mobile phase) before it reaches the pump. A guard column is often placed before the analytical or preparative column; i.e., the primary column. The purpose of such a guard column is to "guard" the primary column by absorbing unwanted sample components that might otherwise bind irreversibly to the analytical or preparative column.

In practice, various components in an LC system may be connected by an operator to perform a given task. For example, an operator will select an appropriate mobile phase and column, and then connect a supply of the selected mobile phase and a selected column to the LC system before operation. In order to be suitable for high performance liquid chromatography (HPLC) applications, each connection must be able to withstand the typical operating pressures of the LC system. If the connection is too weak, it may leak. Because the types of solvents that are sometimes used as the mobile phase are often toxic and because it is often expensive to obtain and/or prepare many samples for use, any such connection failure is a serious concern. A high pressure fitting is further discussed in U.S. patent application Ser. No. 13/038,110 (published as U.S. Patent Publication No. US 2012/0223522 A1), the contents of which are incorporated herein by reference.

Most conventional HPLC systems include pumps which can generate relatively high pressures of up to around 5,000 psi to 6,000 psi or so. In many situations, an operator can obtain successful results by operating an LC system at "low" pressures of anywhere from just a few psi or so up to 1,000 psi or so. More often than not, however, an operator will find it desirable to operate a LC system at relatively "higher" pressures of over 1,000 psi.

Another, relatively newer liquid chromatography form is Ultra High Performance Liquid Chromatography (UHPLC) in which system pressure extends upward to 1400 bar or 20,000 psi. Both HPLC and UHPLC are examples of analytical instrumentation that utilize fluid transfer at elevated pressures. For example, in U.S. Patent Publication No. US 2007/0283746 A1, published on Dec. 13, 2007 and titled "Sample Injector System for Liquid Chromatography," an injection system is described for use with UHPLC applications, which are said to involve pressures in the range from 20,000 psi to 120,000 psi. In U.S. Pat. No. 7,311,502, issued on Dec. 25, 2007 to Gerhardt, et al., and titled "Method for Using a Hydraulic Amplifier Pump in Ultrahigh Pressure Liquid Chromatography," the use of a hydraulic amplifier is described for use in UHPLC systems involving pressures in excess of 25,000 psi. In U.S. Patent Publication No. US 2005/0269264 A1, published on Dec. 8, 2005 and titled "Chromatography System with Gradient Storage and Method for Operating the Same," a system for performing UHPLC is disclosed, with UHPLC described as involving pressures above 5,000 psi (and up to 60,000 psi). Applicants hereby incorporate by reference as if fully set forth herein U.S. Pat. No. 7,311,502 and US Patent Publications Nos. US 2007/0283746 A1 and US 2005/0269264 A1.

Given the desirability of need for leak-free connections, conventional connections have been made with stainless steel tubing and stainless steel end fittings. More recently, however, it has been realized that the use of stainless steel components in a LC system can have potential drawbacks in situations involving biological samples, and cannot be routinely used for ion chromatography. For example, the components in a sample may attach themselves to the wall of stainless steel tubing. This can present problems because the detector's measurements (and thus the chromatogram) of a given sample may not accurately reflect the sample if some of the sample's components or ions remain in the tubing and do not pass the detector. Perhaps of even greater concern, however, is the fact that ions from the stainless steel tubing may detach from the tubing and flow past the detector, thus leading to potentially erroneous results. Hence, there is a need for biocompatible or metal-free connections through the use of a material that is chemically inert with respect to such biological samples and the mobile phase used with such samples, so that ions will not be released by the tubing and thus contaminate the sample. Such connections and tubing are further described in U.S. patent application Ser. No. 13/206,873, the contents of which are incorporated herein by reference.

In many applications using selector/injector valves to direct fluid flows, and in particular in liquid chromatography, the volume of fluids is small. This is particularly true when liquid chromatography is being used as an analytical method as opposed to a preparative method. Such methods often use capillary columns and are generally referred to as capillary chromatography. In capillary chromatography, it is often desired to minimize the internal volume of the selector or injector valve. One reason for this is that a valve having a large volume will contain a relatively large volume of liquid, and when a sample is injected into the valve the sample will be diluted, decreasing the resolution and sensitivity of the analytical method.

Micro-fluidic analytical processes also involve small sample sizes. As used herein, sample volumes considered to involve micro-fluidic techniques can range from as low as volumes of only several picoliters or so, up to volumes of several milliliters or so, whereas more traditional LC techniques, for example, historically often involved samples of about one microliter to about 100 milliliters in volume. Thus, the micro-fluidic techniques described herein involve volumes one or more orders of magnitude smaller in size than traditional LC techniques. Micro-fluidic techniques can typically be expressed as those involving fluid flow rates of about 0.5 ml/minute or less.

As noted, liquid chromatography (as well as other analytical instrument) systems typically include several components. For example, such a system may include a pump, an injection valve or autosampler for injecting the analyte, a precolumn filter to remove particulate matter in the analyte solution that might clog the column, a packed bed to retain irreversibly adsorbed chemical material, the LC column itself, and a detector that analyzes the carrier fluid as it leaves the column Ion chromatography may also utilize a suppressor column to facilitate detection dynamic range. These various components may typically be connected by a miniature fluid conduit, or tubing, such as metallic or polymeric tubing (for ion chromatography), usually having an internal diameter of 0.003 to 0.040 inch.

Fittings for connecting various LC system components and lengths of tubing are disclosed in prior patents, for example, U.S. Pat. Nos. 5,525,303; 5,730,943; and 6,095,572, the disclosures of which are herein all incorporated by reference as if fully set forth herein. The reliability and performance of threaded fluidic fittings is dependent on the amount of torque applied to tighten (or loosen) the fittings. Methods and systems for controlling the torque applied to fittings have been described in U.S. Provisional Patent Application Nos. 61/609,795 and 61/723,163, the contents of which are herein incorporated by reference.

It will be understood by those skilled in the art that, as used herein, the term "LC system" is intended in its broad sense to include all apparatus and components in a system used in connection with a liquid chromatography system (including but not limited to HPLC or UHPLC), and that the discussion of components in the context of LC systems is exemplary, as the invention may apply beyond LC systems to gas and ion chromatography, as well as in vitro diagnostic (IVD) or environmental analysis, and in other analytical instruments (AI) and systems, and may be made of only a few simple components or made of numerous, sophisticated components which are computer controlled or the like. Those skilled in the art will also appreciate that an LC system is one type of an AI system. For example, gas chromatography is similar in many respects to liquid chromatography, but obviously involves a gas sample to be analyzed. Although the following discussion focuses on liquid chromatography, those skilled in the art will appreciate that much of what is said with respect to LC systems also has application to gas chromatography, ion chromatography, and other types of AI systems and methods. Other such AI systems and methods may include, for example, lab on a chip, printing, sensors, micro chromatography, biochemical detection, mass spectrometry, biological sensing, drug discovery, drug delivery, molecular separation, proteomics, fuel cells, optics and opto-fluidics, and research tools.

Upchurch Scientific has marketed "nanoport fittings" for use with MEMS devices, which can further be used with or in LC or other AI systems. These fittings are typically secured to the fluidic chip of the MEMS by gluing the fay surface interface between the chip and the fitting, and then clamping the fitting to the chip while the epoxy cures.

Gluing and clamping processes can suffer the disadvantages of being cumbersome, and with fittings that are too large, difficult to align, and not reusable. Standard fitting designs—such as those using ferrules, lock rings, and seal rings—can be difficult to incorporate into interconnects for MEMS devices due to the chip materials used, miniaturization of feature sizes, and the impact of tolerances on such small parts.

Another challenge is that some MEMS chips allow access to only one side of the chip. This can be due to, for example, electronics, line of sight, or insulating materials on the opposite face. These chips generally require minimal tube insertion forces, due to a lack of structural support on the opposing side.

SUMMARY OF THE INVENTION

The present disclosure overcomes one or more deficiencies of the prior art by providing a microfluidic interconnect, which can be a component of an analytical instrument (AI) system (such as liquid chromatography), or can be used to connect other components to each other in an AI system. The microfluidic interconnect comprises a reverse-taper port and a seal. In one embodiment, the port has a first port end, a second port end, and an inner port surface with a tapered portion. In certain embodiments, the entire port surface is tapered, while in other embodiments the port surface includes both a tapered portion and a non-tapered portion. In certain embodiments, the tapered portion of the inner surface of the port is at an angle within a range of approximately 80 degrees and approximately 89 degrees with respect to the second port end. Each port end has an opening with a diameter, and in certain embodiments, the diameter of the first port end is smaller than the diameter of the second port end. In certain embodiments, each port diameter is less than 1 inch.

In one embodiment, the seal has a first end and a second end, and each seal end has a rim and an opening with an inner diameter and an outer diameter. The seal also has an inner surface and an outer surface, and in certain embodiments, each surface has a tapered portion. In certain embodiments, the entire seal inner surface is tapered, while in other embodiments, the seal inner surface includes both a tapered and a non-tapered portion. In certain embodiments, the entire seal outer surface is tapered, while in other embodiments, the seal outer surface includes both a tapered and a non-tapered portion. In certain embodiments, the tapered portion of the inner seal surface is at an angle within a range of approximately 91 degrees and approximately 100 degrees with respect to the second seal end. In certain embodiments, the tapered portion of the outer seal surface is at an angle within a range of approximately 95 degrees and approximately 110 degrees with respect to the second seal end.

In certain embodiments, the inner diameter of the first seal end is equal to or larger than the inner diameter of the second seal end, the outer diameter of the first seal end is equal to or smaller than the outer diameter of the second seal end, and the outer diameter of the second seal end is larger than the outer diameter of each port end. In certain embodiments, insertion of the seal into the port causes a compression of the outer diameter of the second seal end within a range of approximately 2% and approximately 20%.

In certain embodiments, the portion of the seal bound by the seal first end, the seal second end, the seal inner surface, and the seal outer surface is substantially hollow. In other embodiments, the seal has a first end with a rim and an opening, a second end with two openings and two rims, a first inner surface, a first outer surface, a second inner surface, and a second outer surface.

In certain embodiments, a tube is slidably coupled to an inner surface of the seal, and the tube has an outer diameter that is equal to or larger than the inner diameter of the second seal end. In certain embodiments, the seal comprises a fluoro-elastomer. In certain embodiments, the tube comprises polyetheretherketone (PEEK™), polyetheretherketone-covered fused silica (PEEKsil™), stainless steel, or fused silica. The tube and seal can be chemically compatible with respect to water, methyl ethyl ketone (MEK), aliphatic hydrocarbons, and aromatic hydrocarbons. In certain embodiments, insertion of the tube into the seal causes an elongation of the inner diameter of the second seal end within a range of approximately 2% and approximately 20%. In certain embodiments, a frictional force between the seal and the tube exceeds an extrusion force of the tube. In certain embodiments, a thermosetting polymer such as epoxy can be used to couple the seal to the tube.

BRIEF DESCRIPTION OF THE DRAWINGS

FIGS. 12A, 12B, 12C. Perspective views and a sectional side view of another embodiment of a seal.

DETAILED DESCRIPTION

Figure 1:
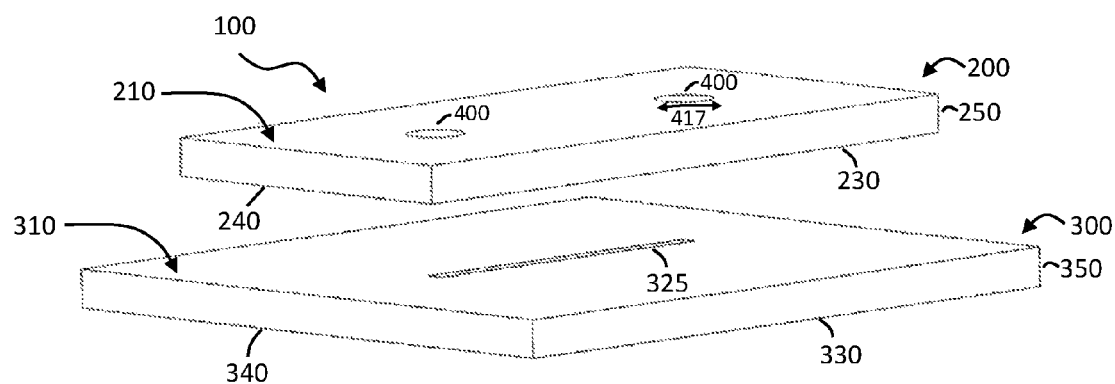
FIG. 1. An exploded perspective view of an exemplary chip.
Figure 2:
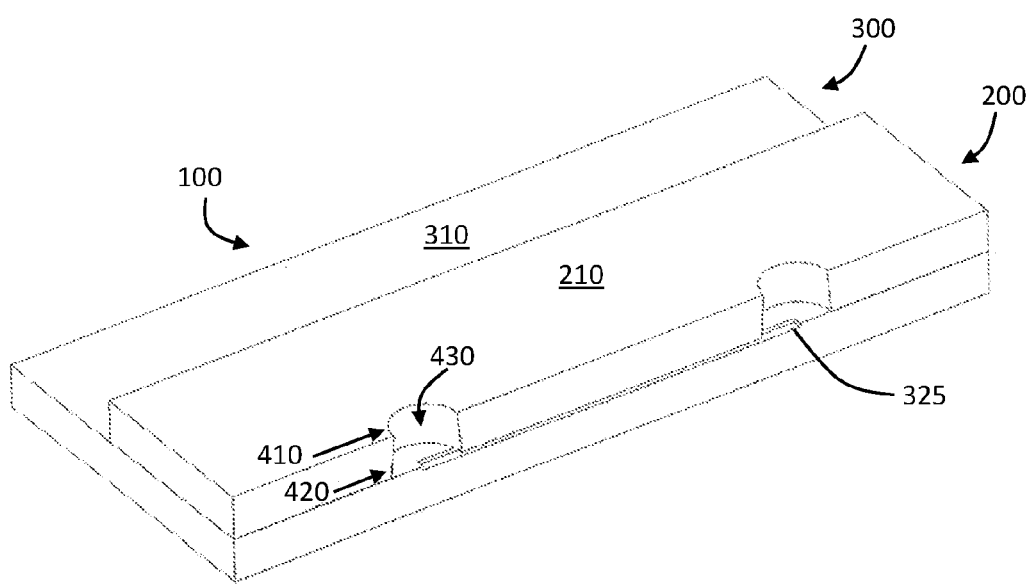
FIG. 2. A sectional perspective view of the exemplary chip of FIG. 1.

Reference is made to FIG. 1 and FIG. 2. FIG. 1 shows an exploded perspective view of an exemplary chip, and FIG. 2 shows a sectional perspective view of the exemplary chip of FIG. 1. In the preferred embodiment, chip 100 comprises two plates: a top plate 200 and a bottom plate 300. Top plate 200 has a top face 210 and a bottom face 220, and bottom plate 300 has a top face 310 and a bottom face 320. Top plate 200 and bottom plate 300 have respective lengths 230 and 330, respective widths 240 and 340, and respective thicknesses 250 and 350. In the preferred embodiment, the top plate and bottom plate have substantially the same dimensions, but those of skill in the art will appreciate that they may choose a top plate 200 and a bottom plate 300 with different dimensions. Plates 200 and 300 are each preferably made of a hard material, such as borosilicate glass (Pyrex), though they can also be made of softer materials, such as plastic. Standard thicknesses of borosilicate glass chips are, for example, 1.1 min (0.043 inch), 0.55 mm (0.022 inch), and 0.50 mm (0.020 inch). Those of skill in the art will appreciate that a solution for hard chips will also work for softer chips, since the processing options and capabilities are broader for soft chips.

Figure 3:
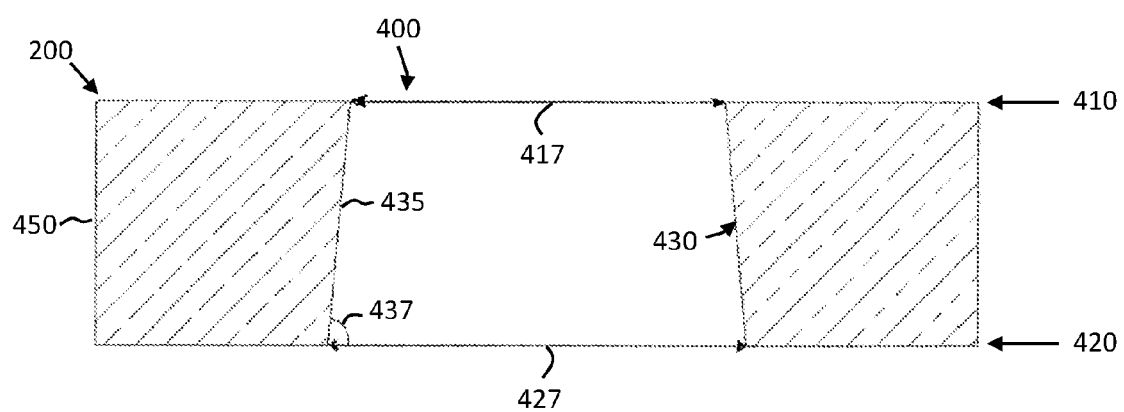
FIG. 3. A sectional side view of an exemplary port.

FIG. 3 shows a sectional side view of an exemplary port. As can be seen in FIGS. 2 and 3, port 400 has a first port end 410 and a second port end 420. In the preferred embodiment, the two port ends are substantially parallel to one another, distally located from one another, and each with a substantially circular cross-section. The first port end has an opening 415, and the second port end has an opening 425 (not labeled in the figures), the two openings defining a passageway through port 400. The port has a height 450, which in the preferred embodiment approximately equals the thickness 250 of the top plate. The opening at the first port end has a diameter 417 (as also shown in FIG. 1), and the opening at the second port end has a diameter 427, with diameter 417 preferably smaller than diameter 427. In the preferred embodiment, the top plate has two ports with the same general shape and dimension, but those of ordinary skill in the art will appreciate that they may choose ports 400 with differing shapes and dimension.

Referring to FIGS. 2 and 3, port 400 has an inner surface 430. The inner surface of the port has a tapered portion 435. In the preferred embodiment, the entire port is tapered, but those of skill in the art will appreciate that they may choose a port with tapering in less than the entirety of the port. Although the port is preferably frusto-conical in shape, those of skill in the art will appreciate that they could alternatively choose different shapes for the port, such as rectangular. A port taper angle 437 is illustrated between the tapered portion of the port 435 and the second port end 420. By way of convention, port taper angle 437 is less than or equal to 90°.

As shown in FIGS. 1 and 2, ports can be fluidly coupled with one another via fluid channel 325. In fabricating chip 100, the bottom plate has a fluid channel 325, and the top plate 200 has two ports (as shown in FIGS. 1 and 2). However, the top plate 200 can also include more than two ports or less than two ports, and ports can also be included in the bottom plate. After the ports and fluid passages are fabricated, chip 100 is assembled from the top plate 200 and the bottom plate 300 by securing face 220 to face 310. In the preferred embodiment, the two plates are thermally bonded to each other, such as at a relatively high temperature, for example, around 1200° F. (650° C.) or so. Those of ordinary skill in the art would appreciate that they may use other methods to secure the plates 200 and 300 together.

Ultrasonic milling is the preferred method to create the ports 400 and fluid channel 325. These geometries are typically created using a tool with three axes of motion. Other fabrication tools can be used, such as laser ablation and chemical etching, each of which is well-known to those of skill in the art. Fluidic interconnects are generally dependent on the surface finish of mating parts. For elastic seals in the 70 durometer range (shore A), a surface finish of 0.20-0.81 µm (7.9-32 microinch) is typically required. Ultrasonic milling of glass on average produces a surface finish of 2-3 µm (79-118 microinch). Optimizing this process can produce a surface finish in the 0.5-1.5 µm (20-60 microinch) range. The surface finish can also be etched using a hydrofluoric solution. This can create surface finishes down to the 8-20 angstrom (0.0008-0.0020 µm) range, depending on the hydrofluoric concentration used, etch duration and number of parts run per volume of solution. Other processes can also be utilized to produce required surface finishes (e.g. laser ablation, powder blast, etc). Creating appropriate surface finishes on hard chips is well within current process capabilities and known to those of ordinary skill in the art.

The minimum hole diameter produced using standard ultrasonic milling practices is typically ½ mm (0.02 inch), though it is known to those of ordinary skill in the art to fabricate holes in the ¼ mm (0.01 inch) diameter range. Hole tolerances of ±50 µm (0.002 inch) are conventional, though a hole tolerance of ±25 µm (0.001 inch) is well within current process capabilities and known to those of ordinary skill in the art.

Figure 4:
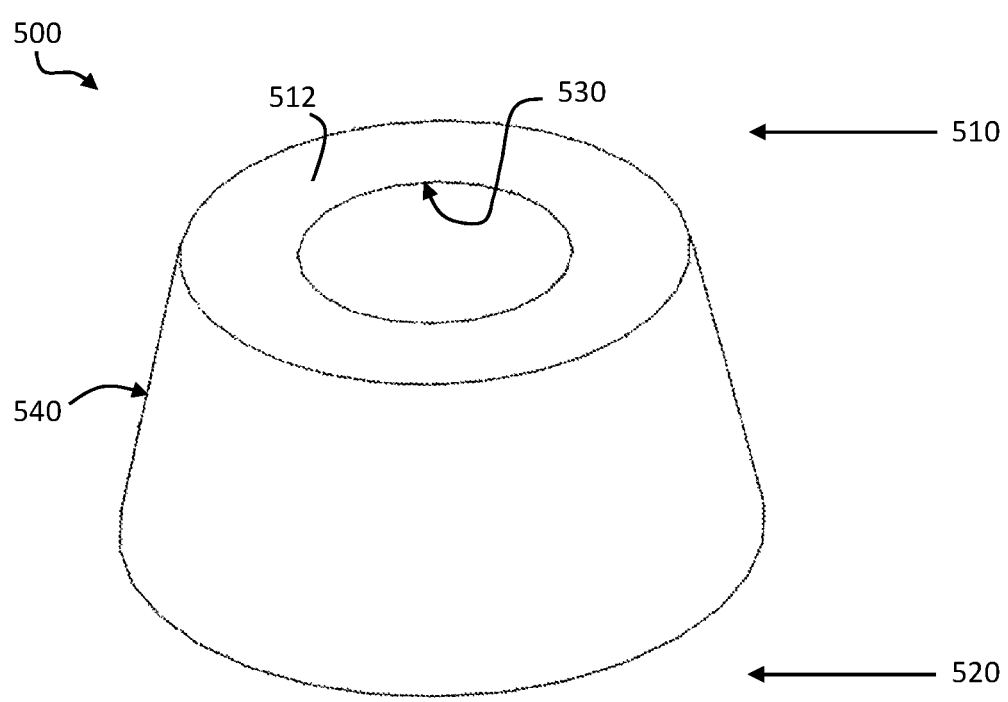
FIG. 4. A perspective view of an exemplary seal.
Figure 5:
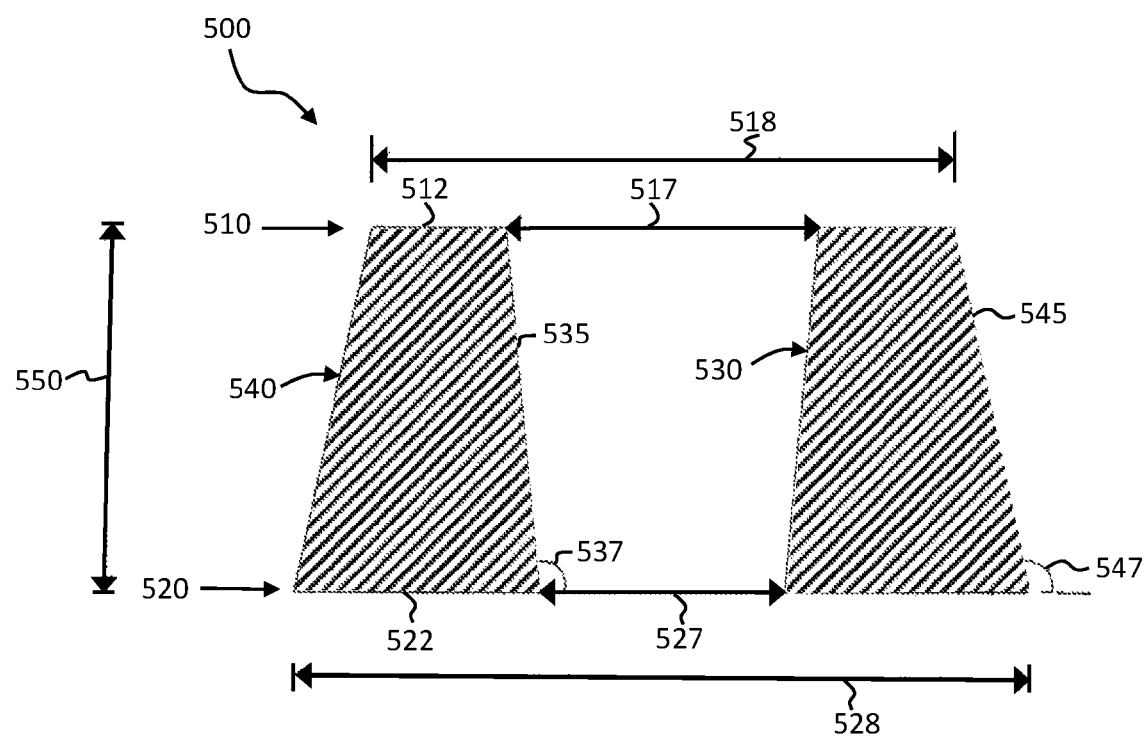
FIG. 5. A sectional side view of the exemplary seal of FIG. 4.

Reference is now made to FIG. 4 and FIG. 5. FIG. 4 shows a perspective view of an exemplary seal, and FIG. 5 shows a sectional side view of the seal. In the preferred embodiment seal 500 is frusto-conical in shape. Seal 500 has a first seal end 510 and a second seal end 520. In the preferred embodiment, the two seal ends are substantially parallel to one another, distally located from one another, and each with a substantially circular cross-section. Seal 500 has a height 550. First seal end 510 has a rim 512 and an opening 515 (not labeled in FIGS.), and second seal end 520 has a rim 522 and opening 525 (not labeled in FIGS.). Seal 500 has an inner seal surface 530 and an outer seal surface 540.

First seal end 510 and its corresponding opening 515 have an inner diameter 517, which represents the maximum width of the first end opening 515 in a nominal state (i.e., prior to the seal being inserted into a port, and prior to a tube being inserted into a seal). First seal end 510 and its corresponding rim 512 also have an outer diameter 518, which represents the maximum nominal width of the first seal end 510. Second seal end 520 and its corresponding opening 525 have an inner diameter 527, which represents the maximum nominal width of the second end opening 525. Second seal end 520 and its corresponding rim 522 have an outer diameter 528, which represents the maximum nominal width of the second seal end 520. Inner diameter 517 is preferably larger than or substantially equal to inner diameter 527, and outer diameter 518 is smaller than or substantially equal to outer diameter 528. In the preferred embodiment, seal second end 520 has an outer diameter 528 with a nominal value that is approximately three times (3×) larger than seal second end inner diameter 527. Preferably, seal second end outer diameter 528 is larger than each of port opening diameter 417 and port opening diameter 427.

As shown in FIGS. 4 and 5, seal inner surface 530 has a tapered portion 535, and seal outer surface 540 has a tapered portion 545. In the preferred embodiment, the entire inner surface 530 and seal outer surface 540 are tapered, but those of skill in the art will appreciate that they may choose to include a non-tapered portion in the seal inner surface and/or the seal outer surface. A seal inner surface taper angle 537 is illustrated between the tapered portion of the seal inner surface 535 and the seal second end 520. A seal outer surface taper angle 547 is illustrated between the tapered portion of the seal outer surface 545 and the seal second end 520. By way of convention, the seal inner surface taper angle 537 and the seal outer surface taper angle 547 are each greater than or equal to 90°.

Seal 500 is preferably molded from a fluoro-elastomer material, such as perfluoroelastomer (FFKM) or tetrafluoroethylene/propylene rubbers (FEPM). FFKM and perflouropolyether (PFP) have good chemical compatibility characteristics and they have relatively low compression set. They also are softer (70-90 durometer range (shore A)) and therefore have better sealing capabilities. FFKM (with trade names of Kalrez®, Simraz, Isolate®, Perlast®, Chemraz®, etc) is a more commonly used material than PFP, although FFKM is typically more expensive than PFP. Other materials for the seal could include FKM or a HiFluor™, such as HF355 available from Parker Hannifin Corp., which is typically more affordable than FFKM.

Figure 6:
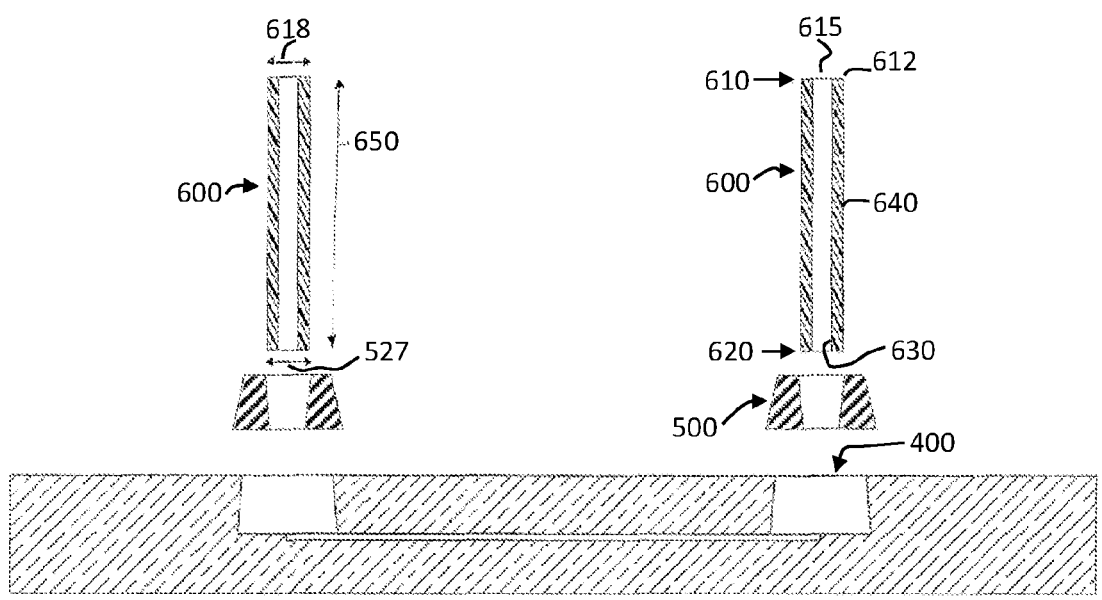
FIG. 6. An exploded sectional side view of an exemplary microfluidic interconnect, chip, and tube.

FIG. 6 shows an exploded sectional side view of an exemplary microfluidic interconnect, chip, and tube. Tube 600 is shown having a first tube end 610, a second tube end 620, and a tube length 650. Tube first end 610 has a rim 612 and an opening 615, and tube second end 620 has a rim 622 and opening 625 (not labeled in FIG. 6). Tube 600 has an inner tube surface 630 and an outer tube surface 640. Tube 600 and its corresponding openings 615 and 625 have an inner diameter 617 (not labeled in FIG. 6), which represents the maximum nominal width of the openings. Tube 600 has an outer diameter 618, which represents the maximum nominal width of the tube. In the preferred embodiment, tube outer diameter 618 is larger than or substantially equal to the inner diameter of the second seal end 527.

In the preferred embodiment, tube 600 is manufactured from polyetheretherketone (PEEK™) or polyetheretherketon-covered fused silica (PEEKsil™), but the tube 600 can also be manufactured from other materials, such as fused silica or stainless steel or any other plastic. PEEK™ tubes are typically manufactured with an outer diameter of: 1/16 inch and a tolerance of ±0.001 inches; 1/32 inch and a tolerance of ±0.005 inch; 510 μm and a tolerance±0.001 inch; or 368 μm and a tolerance±0.0004 inch. PEEKsil™ tubes are typically manufactured with an outer diameter of 1/16 inch and a tolerance off 30 μm; 1/32 inch and a tolerance of ±20 μm; or 360 μm and a tolerance off 10 μm. Fused silica tubing is typically manufactured with an outer diameter of 363 μm and a tolerance of ±10 μm.

In the preferred embodiment, tube inner surface 630 is designed to be in fluidic contact with the fluid destined to be conducted through fluid channel 325. Those of skill in the art will appreciate that they may fabricate the tube 600 from different materials. For example, the outer tube surface 640 may be fabricated out of stainless steel, while the inner tube surface 630 may be fabricated out of a metal-free material such as PEEK™. Such an embodiment may minimize the attachment of sample components to the tube walls. Similarly, such an embodiment may minimize the detachment of ions from the tubing, thereby preventing sample contamination. Such connections and tubing are further described in U.S. patent application Ser. No. 13/206,873 (published as US 2012/0024411 A1), the contents of which are incorporated herein by reference.

Figure 7:
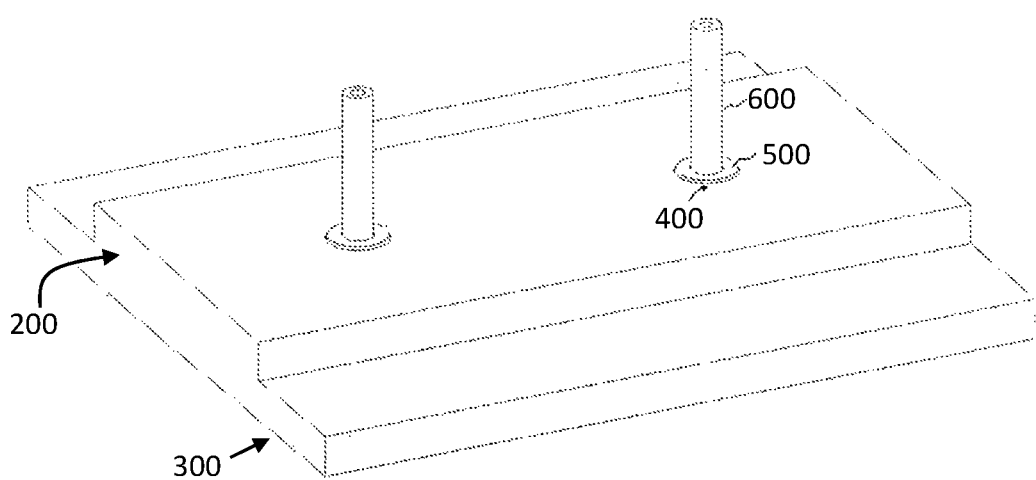
FIG. 7. A perspective view of the exemplary microfluidic interconnect, chip, and tube of FIG. 6.

FIG. 7 shows a perspective view of an exemplary microfluidic interconnect, chip, and tube. Referring to FIGS. 3-7, seal 500 is slidably coupled to the port 400. Seal outer surface 540 has a tapered portion 545 with a tapered angle 547, such that at least the outer diameter of the second seal end 528 is generally compressed as seal 500 is inserted into port 400. Tube 600 is slidably coupled to seal 500. Inner seal surface 530 has a tapered portion 535 with a tapered angle 537, such that at least the inner diameter of the second seal end 527 is generally elongated as tube 600 is inserted into seal 500.

Shown in Table 1 are nominal dimensions used with the seal embodiment of FIG. 5, as sized for 1/32" outer diameter (OD) PEEK™ tubing. In the preferred embodiment, borosilicate glass plates were used with a perfluoroelastomer seal.

TABLE 1

| Item | Description | Dimension |
|------|-------------|-----------|
| 417 | Port first end opening diameter | 0.067 inch |
| 427 | Port second end opening diameter | 0.075 inch |
| 437 | Port taper angle | 84.6 degrees |
| 450 | Port height | 0.040 inch |
| 517 | Seal first end inner diameter | 0.035 inch |
| 518 | Seal first end outer diameter | 0.064 inch |
| 527 | Seal second end inner diameter | 0.027 inch |
| 528 | Seal second end outer diameter | 0.0810 inch |
| 537 | Seal inner surface taper angle | 95.4 degrees |
| 547 | Seal outer surface taper angle | 102.0 degrees |
| 550 | Seal height | 0.040 inch |

The reverse taper angle of the port 400 allows the seal 500 to be wedged into place when the port 400 is pressurized. This action helps to create a good fluidic seal and to counter seal extrusion forces due to pressure. A cup configuration on the second seal end 520 may improve the port-seal interface. Friction between the seal 500 and the tube 600 helps counter tube extrusion during pressurization. At maximum operating pressure the tube frictional force on the seal 500 can exceed the extrusion force of the tube 600.

Shearing of FFKM material during tube insertion is also a risk. The use of alcohol or other chemicals in the port to serve as a lubricant and a twisting motion of the tube 600 during insertion may reduce this shearing action on the seal 500. Alternatively, to facilitate tube insertion, the tube 600 can include a slight radius or chamfer on the end 620 of the tube. This could be considered for use as a "quick change" fitting if it is found that an epoxy set operation is not needed. Inserting an o-ring into the port 400 may be another option, in which the o-ring may be sized specifically for the tube 600. If the friction force is found to be inadequate, or to prevent o-ring roll in the pocket, a user may apply a thermosetting polymer (such as epoxy) to the port/seal/tube interface. The epoxy could flow into the void between the seal 500 and the port 400 as well as the tube 600 to lock the components in place when cured.

The microfluidic interconnect disclosed herein advantageously is low-cost, has a small footprint, and minimizes leaks and dead volume. Similarly, it is compatible with a broad range of process conditions and chemicals, including high pressures (e.g., 500 psig) and elevated temperatures (e.g., 130° F.). For example, those of skill in the art will appreciate that they may construct the microfluidic interconnect from materials that are compatible with methyl-ethyl-ketone (MEK), alcohol, acid, water, aliphatic hydrocarbons, aromatic hydrocarbons, and polar and non-polar solvents. Alternatively, those of skill in the art will appreciate that they may select a specific seal to be used for a specific chemical group, and the seal can be changed out when the chemical group is changed.

The microfluidic interconnect disclosed herein is advantageously compatible with a wide variety of chip materials, including but not limited to borosilicate glass (e.g., Pyrex), poly-methyl-methacrylate (PMMA), polydimethylsiloxane (PDMS), silicon, cyclic olefin copolymer (COC), polycarbonate, and acrylic. In addition, a specific seal can be used for a specific chip material, and the seal can be changed out when the chip material is changed.

The microfluidic interconnect disclosed herein advantageously does not require access to both sides of a chip, such that fittings may be used on a standalone chip or a PCB mounted chip. The interconnect is preferably capable of being used on the end or the face of the chip, provided that the proper port can be fabricated. Similarly, the interconnect will preferably not place excessive loads on tubes which would cause failure.

Those of ordinary skill in the art will appreciate that they may adjust port diameters, port taper angle, port height, seal height, seal outer diameters, and seal outer surface taper angle to account for proper port-seal configuration for proper sealing under pressure. For example, if the entirety of port inner surface 430 comprises a tapered portion 435 with a trapezoidal cross-section, the difference between port first end opening diameter 417 and port second end opening diameter 427 can be calculated as: 2*[port height 450]/[tangent(port taper angle 437)].

As another example, if the entire seal outer surface 540 comprises a tapered portion 545 with a trapezoidal cross-section, the difference between seal first end outer diameter 518 and seal second end outer diameter 528 can be calculated as: 2*[seal height 550]/[tangent(180°−(seal outer surface taper angle 547))].

As yet a further example, if the entire seal inner surface 530 comprises a tapered portion 535 with a trapezoidal cross-section, the difference between seal first end inner diameter 517 and seal second end inner diameter 527 can be calculated as: 2*[seal height 550]/[tangent(180°−(seal inner surface taper angle 537))].

When seal 500 is inserted into port 400, the seal second end outer diameter 528 is typically compressed. A percentage compression can be calculated by: (i) determining the difference in the seal second end outer diameter before and after insertion into the port; and then (ii) dividing that difference by the seal second end outer diameter before insertion into the port. Assuming that the port material (e.g., borosilicate glass, BSG) is generally incompressible as compared to the seal material (e.g., FFKM), the above calculation reduces to: i) subtracting the port second end opening diameter 427 from the seal second end outer diameter 528; and then (ii) dividing that difference by the seal second end outer diameter 528. Using the dimensions provided in table 1 for a BSG port and an FFKM seal, insertion of the seal into the port causes a compression of the seal second end outer diameter by approximately 7.4%. Those of ordinary skill in the art will appreciate that additional compression (or less compression) can be achieved by adjusting the dimensions of the port and seal.

Those of ordinary skill in the art will understand and appreciate that they can adjust seal height, seal inner diameters, seal inner taper angle, and tube outer diameter to account for proper seal-tube configuration for proper sealing under pressure. When tube 600 is inserted into seal 500, the seal second end inner diameter 527 is typically elongated. This elongation can be calculated by: (i) determining the difference in the seal second end inner diameter before and after tube insertion; and then (ii) dividing that difference by the seal second end inner diameter before tube insertion. Assuming that the tube material (e.g., stainless steel or PEEK™) is generally incompressible as compared to the seal material (e.g., FFKM), the above calculation reduces to: i) subtracting seal second end inner diameter 527 from the tube outer diameter 618; and then (ii) dividing that difference by the seal second end inner diameter 527. Using the dimensions provided in table 1 for a ⅟₃₂" OD stainless steel tube and an FFKM seal, insertion of the tube into the seal causes an elongation of the seal second end inner diameter by approximately 15.7%. Those of ordinary skill in the art will appreciate that additional elongation (or less elongation) can be achieved by adjusting the dimensions of the seal and/or using a different size tube.

Figures 8A, 8B, 8C:
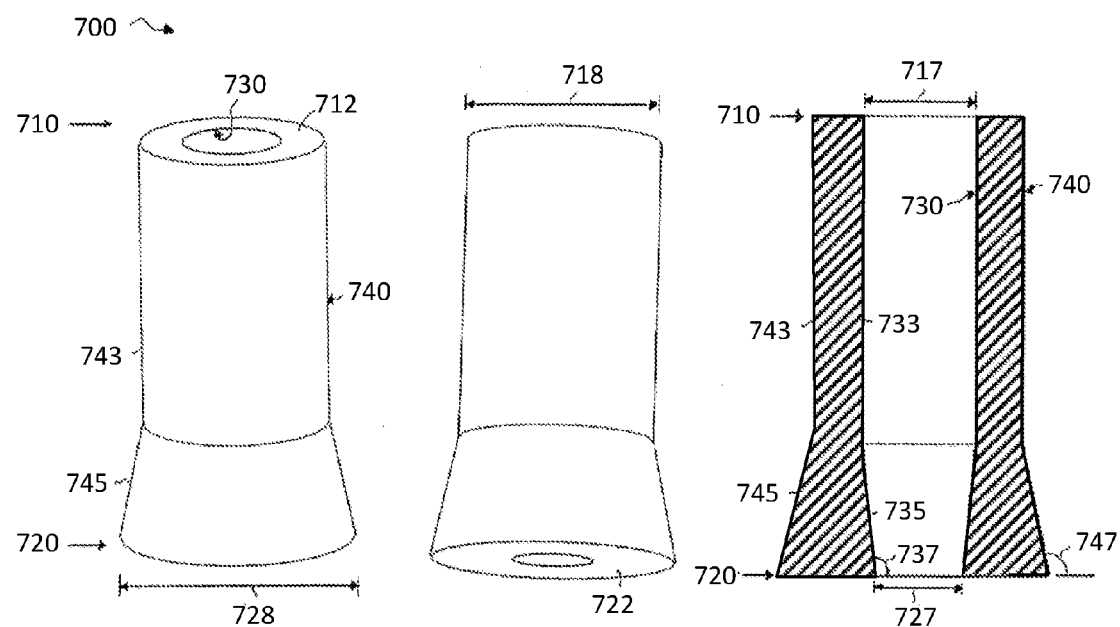
FIGS. 8A, 8B, 8C. Perspective views and a sectional side view of another embodiment of a seal.

Reference is now made to FIGS. 8A, 8B, and 8C. FIG. 8A and FIG. 8B show perspective views of another exemplary seal, and FIG. 8C shows a sectional side view. Seal 700 has a first seal end 710 and a second seal end 720. Seal 700 has a height 750 (not labeled in FIGS.). First seal end 710 has a rim 712 and an opening 715 (not labeled in FIGS.), and second seal end 720 has a rim 722 and opening 725 (not labeled in FIGS.). Seal 700 has an inner seal surface 730 and an outer seal surface 740. First seal end 710 and its corresponding opening 715 have an inner diameter 717, which represents the maximum nominal width of the first end opening 715. First seal end 710 and its corresponding rim 712 also have an outer diameter 718, which represents the maximum nominal width of the first seal end 710. Second seal end 720 and its corresponding opening 725 have an inner diameter 727, which represents the maximum nominal width of the second end opening 725. Second seal end 720 and its corresponding rim 722 have an outer diameter 728, which represents the maximum nominal width of the second seal end 720. Inner diameter 717 is preferably larger than or substantially equal to inner diameter 727, and outer diameter 718 is smaller than or substantially equal to outer diameter 728. Preferably, seal second end outer diameter 728 is larger than each of port opening diameter 417 and port opening diameter 427.

Still with reference to FIGS. 8A, 8B, and 8C, seal 700 has an internal and an external taper. Seal inner surface 730 has a tapered portion 735 and a non-tapered portion 733, and outer seal surface 740 has a tapered portion 745 and a non-tapered portion 743. A seal inner surface taper angle 737 is illustrated between the tapered portion of the seal inner surface 735 and the seal second end 720. A seal outer surface taper angle 747 is illustrated between the tapered portion of the seal outer surface 745 and the seal second end 720. By way of convention, the seal inner surface taper angle 737 and the seal outer surface taper angle 747 are each greater than or equal to 90°.

Figure 9:
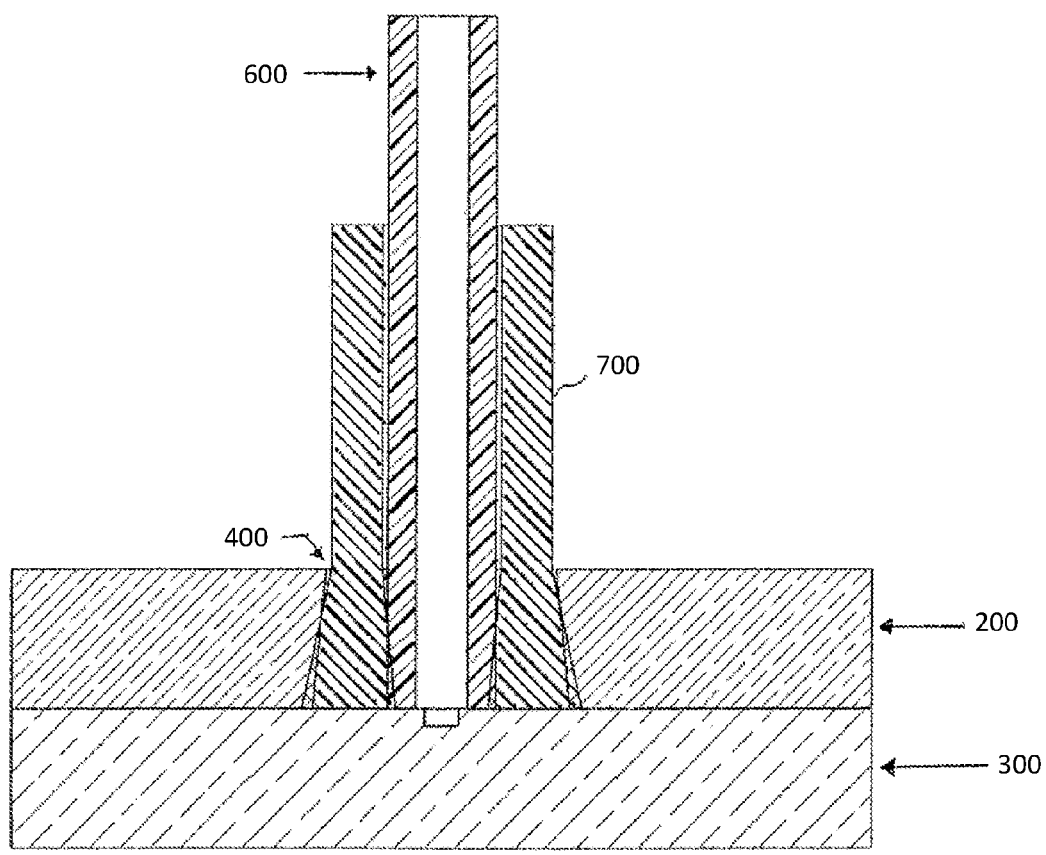
FIG. 9. A sectional side view of another exemplary microfluidic interconnect, chip, and tube.
Figure 10:
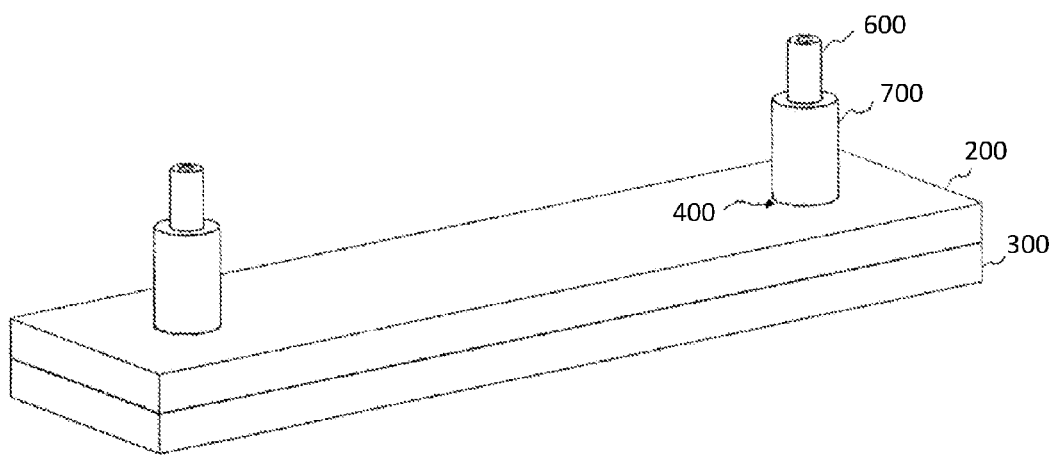
FIG. 10. A perspective view of the exemplary microfluidic interconnect, chip, and tube of FIG. 9.

Shown in FIGS. 9 and 10 are a sectional side view and a perspective view, respectively, of an exemplary microfluidic interconnect, chip, and tube. With reference to FIGS. 8-10, upon insertion of seal 700 into port 400, seal second end opening outer diameter 728 is compressed to provide an interference fit. In FIG. 9, the port, seal, and tube are illustrated in an uncompressed state, such that the seal compression (from the port) and seal elongation (from the tube) can be seen. Upon insertion of tube 600 into seal 700, seal second end opening inner diameter 727 is elongated. The non-tapered portion 733 acts as a sleeve to help retain tube 600 and counter tube extrusion forces. The sleeve portion 733 may allow the microfluidic interconnect, chip, and tube 600 to operate at elevated pressures, compared to an embodiment without the sleeve. The embodiment of FIGS. 8-10 advantageously provides increased surface area in contact between the tube and the seal, thereby allowing increased gluing, mechanical clamping, or other retention mechanisms to be used to provide additional reactance against tube extrusion forces. The sleeve has the additional advantage of minimizing tube bending and twisting.

Figures 11A, 11B:
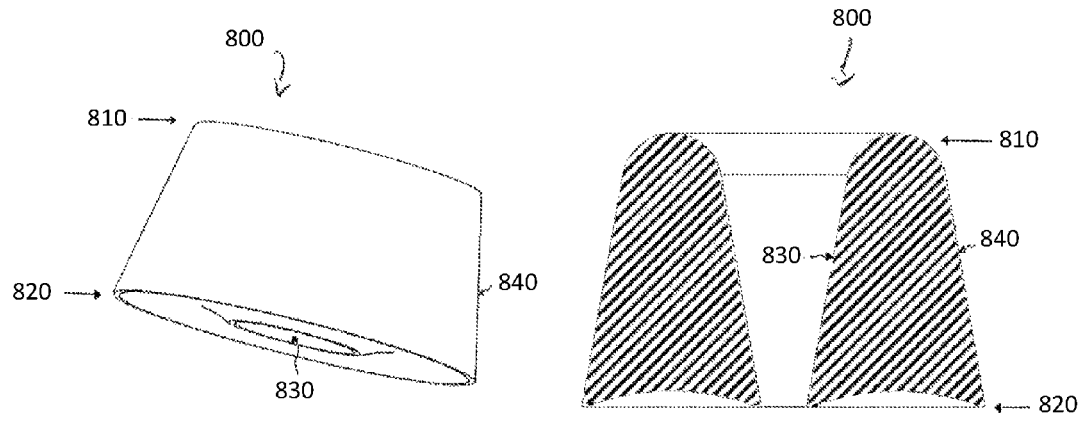
FIGS. 11A, 11B. A perspective view and a sectional side view of another embodiment of a seal.

Shown in FIGS. 11A and 11B are a perspective view and a sectional side view, respectively, of another exemplary seal. Seal 800 is shaped generally similar to seal 500 (shown in FIGS. 4 and 5), except that the portion of the seal bound by seal first end 810, seal second end 820, seal inner surface 830, and seal outer surface 840 is substantially hollow. As compared to a substantially non-hollow embodiment, the embodiment of seal 800 is generally more compressible and thus generally requires less force to insert a tube. Similarly, seal 800 is generally easier to install in a port.

Shown in FIGS. 12A, 12B, and 12C are perspective views and a sectional side view, respectively, of another exemplary seal. Seal 900 has a first end 910, a second end 920, a first inner surface 930, a first outer surface 931, a second inner surface 941, and a second outer surface 940. Seal first end 910 has a first end rim 912 and a first end opening 915. Seal second end 920 has a first rim 922 and first opening 925, and a second rim 923 and second opening 926. Seal 900 has a height 950 (not labeled in FIGS.) Seal first end 910 and its corresponding opening 915 have an inner diameter 917, which represents the maximum nominal width of the first opening 915. First seal end 910 and its corresponding rim 912 also have an outer diameter 918, which represents the maximum nominal width of the first seal end 910. Seal second end 920 and its corresponding first opening 925 have an inner diameter 927, which represents the maximum nominal width of the second opening 925. Second seal end 920 and its corresponding rim 923 have an outer diameter 928, which represents the maximum nominal width of the second seal end 920. Inner diameter 917 is preferably larger than or substantially equal to inner diameter 927, and outer diameter 918 is smaller than or substantially equal to outer diameter 928. Preferably, seal second end outer diameter 928 is larger than each of port opening diameter 417 and port opening diameter 427. Seal 900 includes an internal and an external taper. First inner seal surface 930 has a tapered portion 935, and second outer seal surface 940 has a tapered portion 945. A seal inner surface taper angle 937 is provided between tapered portion 935 and the seal second end 920. A seal outer surface taper angle 947 is provided between tapered portion 945 and the seal second end 920. By way of convention, the seal inner surface taper angle 937 and outer surface taper angle 947 are greater than or equal to 90.degree. As compared to a substantially non-hollow embodiment, the embodiment of seal 900 is generally more compressible and thus generally requires less force to insert a tube. Similarly, seal 900 is generally easier to install in a port. Seal 900 is preferably made from a thereto-plastic material, such as ETFE (Tefzer), PCTFE (Kel-n, or PEEK™)

Although the drawings are illustrated with seals and ports being preferably frusto-conical in shape, and with tubes being preferably cylindrical in shape, those of ordinary skill in the art will appreciate that they may choose other shapes. For example, the openings of the ports and seals can be elliptical, rectangular (including square), and other shapes. Similarly, the tube need not be cylindrical. Thus, the term "diameter" as used in the present disclosure is not limited to a strict circular diameter, but can also include other maximum characteristic dimensions, such as the major axis of an ellipse or the diagonal length of a rectangle.

While the disclosure has shown and described various embodiments, those skilled in the art will appreciate from the drawings and the foregoing discussion that various changes, modifications, and variations may be made without departing from the spirit and scope of the invention as set forth in the claims. Hence the embodiments shown and described in the drawings and the above discussion are merely illustrative and do not limit the scope of the invention as defined in the claims herein. The embodiments and specific forms, materials, and the like are merely illustrative and do not limit the scope of the invention or the claims herein.

I claim:

1. A microfluidic interconnect for use with an analytical instrument system, comprising:
   a) a port in a chip for receiving a fluid, wherein said port has a first port end, a second port end, and an inner port surface with a tapered portion, wherein each port end has an opening with a diameter, and further wherein the diameter of the first port end is smaller than the diameter of the second port end;
   b) a seal having a passageway therethrough and an outer seal surface slidably coupled to the inner port surface, a first seal end, a second seal end, and an inner seal surface,
      i) wherein each seal surface has a tapered portion,
      ii) wherein each seal end has a rim and an opening with an inner diameter and an outer diameter,
      iii) and further wherein the inner diameter of the first seal end is larger than the inner diameter of the second seal end, the outer diameter of the first seal end is smaller than the outer diameter of the second seal end, and the outer diameter of the second seal end in an uncompressed state is larger than the outer diameter of each port end, and wherein the second seal end sealingly engages with the second port end without an additional clamping device when an end portion of an outer surface of a tube which has an outer diameter that is equal to or larger than the inner diameter of the second seal end is coupled to a portion of the inner seal surface and is located within the passageway of said seal within said port.

2. The microfluidic interconnect according to claim 1, wherein said tube comprises polyetheretherketone (PEEK™), polyetheretherketone-covered fused silica (PEEKsil™), stainless steel, or fused silica.

3. The microfluidic interconnect according to claim 1, further comprising a thermosetting polymer for coupling the seal to the tube.

4. The microfluidic interconnect according to claim 1, further comprising a thermosetting polymer for coupling the seal to the port.

5. The microfluidic interconnect according to claim 1, wherein a frictional force between said seal and tube exceeds an extrusion force required to extrude the tube from said seal.

6. The microfluidic interconnect according to claim 1, wherein the tube and seal are chemically compatible with respect to each of water, methyl ethyl ketone, aliphatic hydrocarbons, and aromatic hydrocarbons.

7. The microfluidic interconnect according to claim 1, wherein insertion of the tube into the seal causes an elongation of the second seal end inner diameter within a range of approximately 4% and approximately 35%.

8. The microfluidic interconnect according to claim 1, wherein the diameter of each port opening is less than 1 inch.

9. The microfluidic interconnect of claim 1, wherein said seal comprises a fluoro-elastomer.

10. The microfluidic interconnect of claim 1, wherein said seal and said port are each generally frusto-conical in shape.

11. The microfluidic interconnect according to claim 1, wherein the tapered portion of the inner seal surface is at an angle within a range of approximately 91 degrees and approximately 100 degrees with respect to the second seal end.

12. The microfluidic interconnect according to claim 1, wherein the tapered portion of the inner surface of the port is at an angle within a range of approximately 80 degrees and approximately 89 degrees with respect to the second port end.

13. The microfluidic interconnect according to claim 1, wherein the tapered portion of the outer seal surface is at an angle within a range of approximately 95 degrees and approximately 110 degrees with respect to the second seal end.

14. The microfluidic interconnect according to claim 1, wherein insertion of the seal into the port causes a compression of the outer diameter of the second seal end within a range of approximately 1% and approximately 10%.

15. An analytical instrument system comprising at least one microfluidic connection, wherein said microfluidic connection comprises:
   a) a port in a chip, wherein said port has a first port end, a second port end, and an inner port surface with a tapered portion, wherein each port end has an opening with a diameter, wherein the diameter of the first port end is smaller than the diameter of the second port end, wherein the second port end is in fluid communication with a fluid channel in the chip, and wherein said port defines a frusto-conical shape;
   b) a seal having a passageway therethrough, an outer seal surface slidably and removably coupled to the inner port surface, a first seal end, a second seal end, and an inner seal surface, wherein each seal surface has a tapered portion, and wherein an inner diameter of the first seal end is larger than an inner diameter of the second seal end, an outer diameter of the first seal end is smaller than an outer diameter of the second seal end, and the outer diameter of the second seal end in an uncompressed state is larger than the outer diameter of each port end, wherein said seal defines a frusto-conical shape, and wherein the second seal end and the second port end are sealingly engaged; and
   c) a tube having a passageway therethrough and having a first tube end and a second tube end, wherein a portion of said tube is located within the passageway of said seal and within said port, and wherein the second tube end is sealingly engaged with the second port end, and wherein at least a portion of said tube proximal the second tube end has an outer diameter that is equal to or larger than the inner diameter of the second seal end.

16. The analytical instrument system according to claim 15, wherein a frictional force between said seal and tube exceeds an extrusion force required to extrude the tube from said seal.

17. The analytical instrument system according to claim 15, wherein the tube and seal are chemically compatible with respect to each of water, methyl ethyl ketone, aliphatic hydrocarbons, and aromatic hydrocarbons.

18. The analytical instrument system according to claim 15, wherein insertion of the tube into the seal causes an elongation of the second seal end inner diameter within a range of approximately 4% and approximately 35%.

19. The analytical instrument system of claim 15, wherein said seal comprises a fluoro-elastomer.

20. The analytical instrument system according to claim 15, wherein the tapered portion of the inner surface of the port is at an angle within a range of between approximately 80 degrees and approximately 89 degrees with respect to the second port end.

21. The analytical instrument system according to claim 15, wherein the tapered portion of the inner seal surface has an angle within a range of approximately 91 degrees and approximately 100 degrees with respect to the second seal end.

22. The analytical instrument system according to claim 15, wherein the tapered portion of the outer seal surface has an angle within a range of approximately 95 degrees and approximately 110 degrees with respect to the second seal end.

23. The analytical instrument system according to claim 15, wherein the outer diameter of the second seal end is compressed within a range of approximately 1% and approximately 10% when said seal is inserted into the port.

24. A microfluidic fitting assembly comprising:
   a) a port in a chip body, wherein said port has a first port end, a second port end, and an inner port surface with a tapered portion, wherein each port end has an opening with a diameter, and further wherein the diameter of the first port end is smaller than the diameter of the second port end, wherein the second port end is in fluid communication with a fluid channel in the chip body, and wherein said port defines a frusto-conical shape;
   b) a seal having a passageway therethrough, an outer seal surface slidably and removably coupled to the inner port surface, a first seal end, a second seal end, and an inner seal surface, wherein each seal surface has a tapered portion, and wherein an inner diameter of the first seal end is larger than an inner diameter of the second seal end, an outer diameter of the first seal end is smaller than an outer diameter of the second seal end, and the outer diameter of the second seal end in an uncompressed state is larger than the outer diameter of each port end, wherein said seal defines a frusto-conical shape, and wherein the second seal end and the second port end are sealingly engaged; and
   c) a tube having a passageway therethrough and having a first tube end and a second tube end, wherein a portion of said tube is located within the passageway of said seal and within said port, and wherein the second tube end is sealingly engaged with the second port end, and wherein at least a portion of said tube proximal the second tube end has an outer diameter that is equal to or larger than the inner diameter of the second seal end and elongates the inner diameter of the second seal end within a range of 4% to 35%.

25. The microfluidic fitting assembly according to claim 24, wherein said seal comprises a fluoro-elastomer.

26. The microfluidic fitting assembly according to claim 24, wherein the tapered portion of the inner seal surface has an angle within a range of approximately 91 degrees and approximately 100 degrees with respect to the second seal end.

27. The microfluidic fitting assembly according to claim 24, wherein the tapered portion of the outer seal surface has an angle within a range of approximately 95 degrees and approximately 110 degrees with respect to the second seal end.

28. The microfluidic fitting assembly according to claim 24, wherein the outer diameter of the second seal end is compressed within a range of approximately 1% and approximately 10% when said seal is inserted into the port.

29. The microfluidic fitting assembly according to claim 24, wherein a frictional force between said seal and tube exceeds an extrusion force required to extrude the tube from said seal.

30. The microfluidic fitting assembly according to claim 24, wherein the tube and seal are chemically compatible with respect to each of water, methyl ethyl ketone, aliphatic hydrocarbons, and aromatic hydrocarbons.

31. The microfluidic fitting assembly according to claim 24, wherein insertion of the tube into the seal causes an elongation of the second seal end inner diameter within a range of approximately 4% and approximately 35%.

32. The microfluidic fitting assembly according to claim 24, wherein the tapered portion of the inner surface of the port is at an angle within a range of between approximately 80 degrees and approximately 89 degrees with respect to the second port end.

* * * * *